United States Patent [19]

Oxenrider et al.

[11] Patent Number: 4,460,785

[45] Date of Patent: Jul. 17, 1984

[54] ACID CHLORIDE OF PYROMELLITIC ANHYDRIDE

[75] Inventors: Bryce C. Oxenrider, Florham Park; David J. Long, Stanhope, both of N.J.

[73] Assignee: Allied Corporation, Morris Township, Morris County, N.J.

[21] Appl. No.: 429,947

[22] Filed: Sep. 30, 1982

[51] Int. Cl.³ .................... C07C 69/773; C07C 57/72; C07C 153/07

[52] U.S. Cl. ........................................ 560/83; 252/8.6; 252/8.8; 266/455 R; 266/544 N; 560/76; 560/87

[58] Field of Search ........................ 260/455 R, 544 N; 560/76, 83; 252/8.6, 8.8

[56] References Cited

U.S. PATENT DOCUMENTS

| | | | |
|---|---|---|---|
| 4,209,610 | 6/1980 | Mares et al. | 260/40 |
| 4,252,982 | 2/1981 | Oxenrider | 560/87 |
| 4,329,489 | 5/1982 | Saunders et al. | 560/79 |

FOREIGN PATENT DOCUMENTS

| | | |
|---|---|---|
| 1102344 | 6/1981 | Canada . |
| 1543081 | 3/1979 | United Kingdom . |

*Primary Examiner*—Natalie Trousof
*Assistant Examiner*—Vera C. Clarke
*Attorney, Agent, or Firm*—Alan M. Doernberg; Gerhard H. Fuchs; Kenneth E. Stroup

[57] ABSTRACT

Pyromellitate diester-diacid chlorides are disclosed that are useful as intermediates in the synthesis of a variety of soil and water repelling compounds. The pyromellitates of this invention characteristically contain two ester moieties wherein said ester moieties contain a fluorinated or saturated hydrocarbon alkyl moiety. The pyromellitates additionally contain two acid chloride moieties which are capable of reacting with various compounds to produce various products useful as surfactants.

5 Claims, No Drawings

ACID CHLORIDE OF PYROMELLITIC ANHYDRIDE

DESCRIPTION

BACKGROUND OF THE INVENTION

This invention relates to novel benzene diester-diacid chlorides which may be used in the synthesis of soil and water repelling compounds.

U.S. Pat. No. 4,209,610 (Mares et al., 1980) discloses that benzene diacid-diesters may be synthesized by reacting fluorinated alcohols with pyromellitic dianhydride. Upon treatment with epoxide-containing organic radicals, the diacid-diesters react to form partially fluorinated esters of benzene carboxylic acids. The partially fluorinated esters are used as water and soil repellents in various fibers.

The above-referenced patent also discloses that trimesic acid may be converted to trimesoyl trichloride, which in a two step synthesis yields partially fluorinated esters that are useful as soil and water repellents in various fibers. Initially, the synthesis involves treating trimesoyl trichloride with less than a three molar proportion of a fluorinated alcohol. Secondly, the unreacted carboxy chloride groups are converted to the desired ester groups by reaction with the appropriate alcohol.

British Pat. No. 1,543,081 (1979) discloses that fluorinated ester-acids may be synthesized by reacting phthalic anhydride with fluorinated alcohols. The above-referenced British patent further discloses that the resulting ester-acids may be converted to ester-acid chlorides, which in a subsequent step may be reacted with various reagents to form soil and water repelling agents.

Canadian Pat. No. 1,102,344 describes numerous fluorocarbon compounds which are useful as soil and water repelling agents for various fibers. Included amongst these compounds are fluorocarbon esters of phthalic anhydride wherein the ester-acid chloride of phthalic anhydride is used as an intermediate in the synthesis of the fluorocarbon oil and water repelling agents. (Specification pg. 20, lines 18-25).

U.S. Pat. No. 4,252,982 (Oxenrider, 1981) describes an improvement of U.S. Pat. No. 4,209,610 and British Pat. No. 1,543,081. The improvement involves synthesizing the desired fluorinated esters in non-toxic aliphatic esters having a boiling point between about 50° C. and about 150° C., as opposed to synthesizing the fluorinated esters in solvents such as DMF and NMP which pose environmental and product safety hazards.

BRIEF DESCRIPTION OF THE INVENTION

The present invention relates to novel benzene diester-diacid chloride compounds having the structure

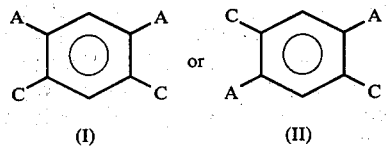

(I)         (II)

or mixtures thereof wherein C is COCl, and A is COWQ with W being —O—, —S—, —NH—, or —N(CH$_3$)—; wherein Q is alkyl of 2-24 carbons or —R—(CF$_2$)$_p$CF$_3$ with R being alkylene of 1-6 carbons and p being an integer of 3-15.

These compounds have unexpectedly been discovered to be extremely desirable intermediates in the synthesis of various soil and water repelling compounds. In particular, pyromellitic dianhydride is initially reacted with fluorocarbon or hydrocarbon alcohols in order to produce benzene diacid-diesters. The desired acid chloride intermediates are then synthesized by reacting the benzene diacid-diester with a suitable chlorinating agent such as thionyl chloride, phosgene-DMF, oxalyl chloride, or phosphorous pentachloride wherein said chlorination agent converts the acid functionality to the acid chloride functionality.

The novel acid chlorides of this invention are useful in the synthesis of fluorocarbon soil and water repellents described in U.S. Pat. No. 4,209,610 (1980). However, of even more importance is the fact that soil and water repelling compounds which could not be synthesized using previously known intermediates may now be easily prepared using the compounds of the present invention as intermediates.

DETAILED DESCRIPTION OF THE INVENTION

The compounds of the present invention are diester-diacid chlorides of pyromellitic dianhydride. In order to prepare the novel acid chlorides, it is initially necessary to convert pyromellitic dianhydride to its diester-diacid. This is accomplished by reacting pyromellitic dianhydride with an appropriate alcohol. The acid chlorides of this invention have the general structure

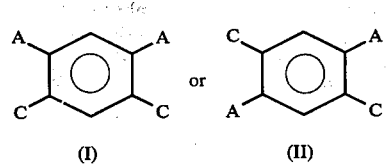

(I)         (II)

or mixtures thereof wherein C is COCl and A is COWQ with W being —O—, —NH—, —S— or —N(CH$_3$)—; wherein Q is alkyl of 2-24 carbons or —R—(CF$_2$)$_p$CF$_3$ with R being alkylene of 1-6 carbons and p being an integer of 3-15.

In view of the above structure, suitable alcohols with which pyromellitic dianhydride may be reacted to synthesize the diacid-diesters include saturated hydrocarbon alcohols having from 2 to 24 carbons, and partially fluorinated alcohols having from 5 to 22 carbons. It will be appreciated that the acid chlorides of this invention also include the diamide-diacid chlorides of pyromellitic dianhydride. In order to synthesize the diamide-diacid chlorides, pyromellitic dianhydride is reacted with saturated hydrocarbon amines or partially fluorinated amines having from 3 to 24 carbons. In the the preferred embodiments of this invention, the alcohols or amines used to synthesize the ester or amide moieties have 4 to 14 carbons.

The desired fluorinated alcohols can be prepared from the corresponding iodide by known methods. For example, fluorinated alcohols can be prepared as described in U.S. Pat. Nos. 3,111,861 (Ahlbrecht, 1965), 3,514,487 (Anello et al., 1970), and 3,646,153 (Oxenrider et al., 1972).

Fluorinated amines for use in synthesizing amides of pyromellitic dianhydrides can be obtained for example by reduction of fluorinated nitriles. See U.S. Pat. No. 3,646,153 at col. 7, lines 10-42.

In the preferred embodiments of this invention, preferred fluorinated acid chlorides are those derived from fluorinated hydrocarbyl ethanols represented by the formula —O—(CH$_2$)$_2$(CF$_2$)$_p$CF$_3$ where p is 3–13. The preferred hydrocarbon acid chlorides are those derived from saturated alkanols having from 14 to 20 carbons. Additionally, W in the above formula is preferrably —O— for both hydrocarbon and fluorinated acid chlorides.

Following preparation of the diester-diacid or the diamide-diacid, said ester-acid or said amide-acid is dissolved in an aliphatic ester having a boiling point between about 50° C. and 150° C. Suitable esters include esters of formic, acetic, propanoic (propionic), butanoic (butyric) and pentanoic (valeric) acids having boiling points between about 50° C. and about 150° C. such as propyl formate, methyl acetate, ethyl acetate, propyl acetate, isobutyl acetate, butyl acetate, pentyl acetate, methyl propionate, ethyl propionate, butyl propionate, methyl butyrate, ethyl butyrate and methyl valerate. Ethyl acetate is especially preferred.

The acid chlorides of the present invention may now be prepared by the addition of a chlorinating agent to the diester-diacid so that the carboxyl moieties are converted to carboxy chloride moieties. Suitable chlorinating agents include oxalyl chloride, phosphorous pentachloride, phosphorous trichloride, phosgene-DMF, and thionyl chloride. In the preferred embodiments of this invention oxalyl chloride is dissolved in ethyl acetate and then this mixture is slowly added to the diester-diacid in order to initiate the reaction which results in the production of the acid chlorides. Dissolving oxalyl chloride in ethyl acetate is done in order to control the temperature during the course of the reaction.

The ratio of the reactants (chlorinating agent/diester-diacid) should be about 2:1 so that theoretically all carboxyl groups will be converted to carboxy chloride functionalities.

The reaction between the chlorinating agent and the diester-diacid should be allowed to continue between about 2 and 5 hours with about 3 hours being the reaction time necessary for complete reaction to occur. The reaction should be conducted between about 40° C. and about 60° C. with about 50° C. being the preferred reaction temperature.

The acid chlorides of the present invention are useful as intermediates in the preparation of a variety of soil and water repelling compounds. The acid chlorides may be advantageously employed as intermediates in the synthesis of many of the soil and water repelling compounds disclosed in U.S. Pat. No. 4,209,610. For instance, compounds having structure A or B or mixtures thereof

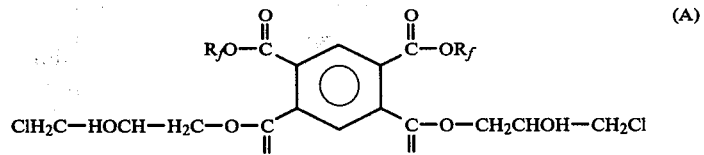

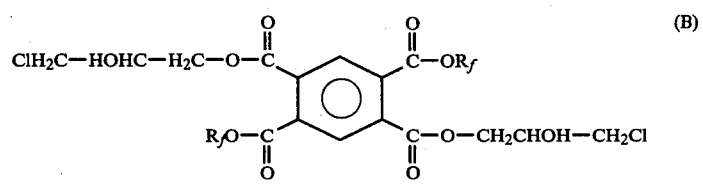

with R$_f$ being a fluorinated alkyl group as disclosed by U.S. Pat. No. 4,209,610 are synthesized by reacting epichlorohydrin with the fluorinated diester-diacid. Epichlorohydrin is an environmentally undesirable material. Compounds having structure A or B above or mixtures thereof above and as defined U.S. Pat. No. 4,209,610 may now be synthesized by reacting the diester-diacid chlorides of the present invention with 3-chloro-1,2-propane diol. Thus, the use of the environmentally unacceptable epichlorohydrin is eliminated.

More importantly, however, soil and water repelling compounds which could not be easily synthesized using previously known intermediates may now be easily synthesized using the novel acid chlorides of the present invention. In particular, soil and/or water repelling monocyclic pyromellitates having siloxyl groups or alkyl groups containing a terminal halogen as disclosed in the copending commonly assigned applications of Oxenrider and Long (Ser. No. 429,946 and Ser. No. 431,452), filed herewith, may be synthesized by reacting the acid chlorides of this invention with siloxy amides or thiols or terminally halogenated alkanols. Examples 2 and 3 of this application illustrate the synthesis of pyromellitates having terminally halogenated alkyl moieties. Example 4 of this application illustrates the synthesis of siloxy pyromellitates wherein the acid chlorides of this invention are utilized as intermediates. The acid chlorides of this invention are also useful in the synthesis of soil and water repelling monocyclic pyromellitates having epoxide groups. Example 5 of this application illustrates the synthesis of said epoxide pyromellitates. Additionally, soil and water repelling polycyclic pyromellitate oligomers which have vastly improved retention properties when applied to various fibers may be synthesized using the compounds of the present invention. In general, the polycyclic pyromellitate oligomers are prepared by reacting the acid chlorides of the present invention with monovalent reactants, R'XH, and divalent reactants, HXRXH, wherein X is —O—, —S—, —N(CH$_3$)— or —NH— with R and R' being as represented in Table 1. Example 6 of this application illustrates the synthesis of polycyclic oligomers wherein the acid chlorides of this invention are used as intermediates.

TABLE I

| R | R' |
|---|---|
| alkylene of 2–6 carbons | —CH$_2$CH(OH)CH$_2$Cl |

TABLE I-continued

| R | R' |
|---|---|
| $CH_2C(CH_2Cl)_2CH_2$ | $-CH_2CH(OH)CH_2Br$ |
| $CH_2C(CH_2Br)_2CH_2$ | $-(CH_2)_mCl$  m = 1-8 |
| 1,3 and 1,4 phenylene | $-(CH_2)_mBr$  m = 1-8 |
| $CH_2C(CH_2OH)_2CH_2$ | $-CH(CH_2Cl)_2$ |
|  | $-CH(CH_2Br)_2$ |
|  | $-CH_2CH\overset{O}{\overset{\diagup\phantom{x}\diagdown}{\phantom{xx}}}CH_2$ |
|  | $-(CH_2)_qSi(OR''')_3$ q = 1-8; R''' = Alkyl of 1-3 carbons |

The structure of the oligomers and their method of synthesis is described more fully in a copending commonly assigned application of Oxenrider and Long (Ser. No. 429,945), filed herewith.

The synthesis of compounds using the acid chlorides of this invention involves reacting the acid chlorides with various alcohols for a period between about 2 and 18 hours at a temperature between about 20° C. and 60° C. in the presence of an acid acceptor such as triethyl amine or pyridine. It is not usually necessary to isolate the acid chloride produced from the diester-diacid. In other words, alcohols may be added directly to the acid chloride reaction mixture in order to produce the desired product. However, when thionyl chloride is utilized as the chlorinating agent to produce the acid chloride, isolation of the acid chloride is necessary in order to remove the sulfur dioxide produced by the chlorinating reaction.

EXAMPLE 1

A mixture of meta and para isomers of the diester of pyromellitic anhydride and a mixture of fluorinated alcohols was prepared and isolated in accordance with the procedures of U.S. Pat. No. 4,252,982 to Oxenrider. This diester can be represented by the formulae:

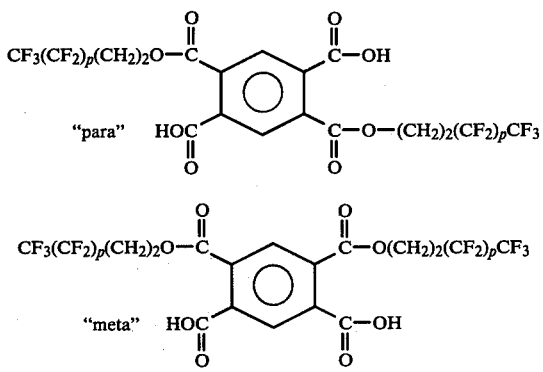

The values for p were 5, 7, 9 and 11 since a mixture of fluorinated alcohols had been used.

A portion of this mixture (50.0 g, 82 meq) was suspended in dry ethyl acetate (250 mL) under nitrogen at 40°-45° C. in a 500 mL round bottom flask. A solution of oxalyl chloride (26.5 mL) was added to the suspension over a period of 30 minutes. Foaming was noted due to a vigorous evolution of gas. The reaction mixture was stirred at 45°-50° C. for 3 hours, cooled to room temperature and flash evaporated. A semi-solid product (52 g) was obtained. The structure of the acid chloride was confirmed by proton NMR.

EXAMPLE 2

A mixture of meta and para isomers of the diester-diacid of pyromellitic anhydride was prepared as in Example 1. A portion of this mixture (5 g, 8.21 meq) was suspended in dry ethyl acetate (15 mL) and DMF (0.1 mol) under a nitrogen atmosphere. The suspension was warmed to 45° C. and a solution of thionyl chloride (0.627 mL, 8.21 meq) in dry ethyl acetate (5 mL) was then added to the suspension over a period of 5 minutes. The reaction mixture was stirred for 3.5 hours at 45° C. The reaction mixture was clear but become cloudy near the end of the reaction. A solution of triethyl amine (1.14 mL, 3.21 meq) in ethyl acetate (5 mL) was added to the diester-diacid chloride product solution, and the resultant solution was stirred for 1 hour. The product solution was filtered and flash evaporated and a semi-solid diester-diacid chloride product (4.9 g) was recovered. The diester-diacid chloride product was dissolved in ethyl acetate (20 mL) and the solution was warmed to 45° C. A solution of 3-chloro-1-propanol (0.6 mL) triethyl amine (1 mL) and ethyl acetate (5 mL) was prepared and added to the diester-diacid chloride product solution over a 5 minute period. The reaction mixture was stirred for 3 hours at a temperature of 45° C., allowed to cool to room temperature and stirred overnight. The product solution was worked up by filtration and flash evaporation. An oil product (4.1 g) was obtained. The product, a pyromellitate with two

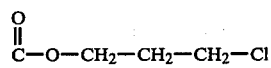

moieties, was confirmed by proton NMR. The product contained some triethyl amine hydrochloride impurities.

EXAMPLE 3

A mixture of meta and para isomers of the diester-acid of pyromellitic anhydride was prepared as in Example 1. A portion of this mixture (10 g, 17.4 meq), DMF (0.5 mL), and ethyl acetate (50 mL) were added to a dry 100 mL flask under a nitrogen atmosphere to form a suspension. The suspension was warmed to 45° C. Gaseous phosgene (2 g, 20.2 meq) was added to the suspension over a period of 15 minutes. The temperature of the suspension increased to 49° C. with the addition of the phosgene. The reaction mixture was stirred and allowed to continue for 2.5 hours at a temperature of 45° C. The diester-diacid chloride product solution was flash evaporated. Vigorous foaming occurred during the final stages of evaporation and all of the solvent could not be removed due to the foaming. A viscous liquid (11.5 g) was obtained. In large scale industrial production it would not be necessary to remove all of the solvents as isolation of the acid chloride would not be necessary in industrial productions.

The liquid was dissolved in dry ethyl acetate (50 mL) and warmed to 45° C. The diester-diacid chlorides of this invention are present in solution at this stage of the example.

A separate reactant mixture of 3-chloro-1-propanol (1.45 mL, 17.4 meq), triethylamine (2.5 mL, 20.2 meq) and dry ethyl acetate (10 mL) was prepared and added to the acid chloride product solution over a period of 15 minutes. The reactant mixture was warmed to 45° C. and stirred for 2 hours. The reactant mixture was allowed to cool to room temperature and stirred overnight. The product solution was filtered and flash evaporated. A viscous liquid product (10.9 g) was obtained. The structure was confirmed by proton and $C^{13}$ NMR.

EXAMPLE 4

A portion of the mixture of meta and para pyromellitate diacid-diesters (5 g, 8.585 meq) of Example 3 and dry ethyl acetate (20 mL) was added to a 100 mL round bottom flask to form a suspension. The suspension was warmed to 45° C. and then a solution of oxalyl chloride (0.8 mL, 8.585 meq) and dry ethyl acetate (10 mL) was added over a period of 20 minutes. The solution was stirred, and the reaction was allowed to continue for a period of 4 hours at a temperature of 45° C. in order to produce the diester-diacid chloride.

The diester-diacid chlorides of this invention are present in solution at this stage of the example. The following description illustrates the further reaction, without isolation of the diesterdiacid chloride to produce a siloxy pyromellitate.

A separate reactant mixture of mercaptopropyl triethoxysilyl (1.88 g, 8.585 meq), triethyl amine (6.65 mL), and dry ethyl acetate (20 mL) was prepared. The diester-diacid chloride product solution was added to this reactant mixture over a period of 20 minutes. The resultant product solution was stirred at 45° C. for 2 hours and then stirred overnight at room temperature. The product solution was filtered and flash evaporated and 3.5 g of a yellow-orange viscous liquid product was recovered. The structure of the siloxy pyromellitate was confirmed by proton NMR. The surface energy of the siloxy pyromellitate was determined to be 14 dynes/cm by the Zisman technique.

EXAMPLE 5

A mixture of meta and para isomers of the diester-diacid of pyromellitic anhydride was prepared as in Example 1. A portion of this mixture (10.0 g, 16.6 meq) was suspended in dry ethyl acetate (45 mL) in a round bottom flask under nitrogen. The suspension was heated at 65° C. for 1 minute and then cooled to 35°–40° C. A solution of oxalyl chloride (3.2 mL, 36 mmol) in ethyl acetate (5 mL) was prepared and added to the suspension over a period of 5 minutes. The reaction mixture was warmed to 40° C., stirred for 2 hours, and then flash evaporated to an orange residue. The diester-diacid chlorides of this invention are present in impure form form at this stage of the example. The following description illustrates the further reaction without purification of the acid chlorides to produce epoxy pyromellitates.

The orange residue was dissolved in dry ethyl acetate (50 mL) and stirred at room temperature under a nitrogen atmosphere. A solution of 2,3-epoxy-1-propanol (1.1 mL, 16.6 mmol), dimethyl pyridine (2.0 mL, 17 mmol), and ethyl acetate (10 mL) was prepared and added to the orange residue above. This reaction mixture was stirred at room temperature for 16 hours. A yellow oil product (14 g) was obtained by filtration and flash evaporation of the reaction mixture. A product having the structure of an epoxy pyromellitate was confirmed by carbon[13] NMR.

EXAMPLE 6

A mixture of meta and para isomers of the diester-diacid of pyromellitic anhydride was prepared as in Example 1. A portion of this mixture of pyromellitate diester (50.0 g, 82 meq) was suspended in 225 mL ethyl acetate at 65° C. for one minute under nitrogen atmosphere in a 500 mL RB flask. The suspension was then cooled to 50° C. Oxalyl chloride (7.2 mL, 83.0 mmol) in 25 mL ethyl acetate was added over 5 minutes and the diester/diacid chloride product solution was stirred at 50° C. for 3 hours. Vigorous evolution of gas was observed. A reactant mixture was separately prepared of 3-chloro-1,2-propanediol (3.5 g, 41.5 mmol), 1,4-butanediol (1.87 mL, 20.8 mmol), triethylamine (23 mL) in ethyl acetate (50 mL). The reactant mixture was then added to the diester/diacid chloride solution over 10 minutes at 50°–60° C. The product solution was then stirred at 60° C. for 18 hours.

The product solution was then worked up by filtering and evaporation on a rotary evaporator. The resultant oil weighed 58 g. Its structure was confirmed by proton and carbon[13] NMR to be a mixture of monocyclic and polycyclic pyromellitates as described in the commonly assigned copending application of Oxenrider and Long (Ser. No. 429,945). The oils had a surface energy of 9 dynes/cm as determined by Zisman procedures.

We claim:

1. A compound having the structure

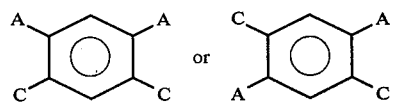

or mixtures thereof wherein C is COCl and A is COWQ with W being —O—, —S—, —NH— or —N(CH3)—; wherein Q is alkyl of 2-24 carbons or —R—(CF2)$_p$CF3 with R being alkylene of 1–6 carbons and p being an integer of 3–15.

2. Compound of claim 1 wherein W is —O—.

3. Compound of claim 1 wherein Q is alkyl of 2-24 carbons.

4. Compound of claim 3 wherein Q is alkyl of 14–20 carbons.

5. Compound of claim 1 wherein Q is —(CH2)2 (CF2)$_p$CF3 and p is 3–13.

* * * * *